(12) United States Patent
Cai et al.

(10) Patent No.: US 6,837,976 B2
(45) Date of Patent: *Jan. 4, 2005

(54) DISPOSABLE SENSOR WITH ENHANCED SAMPLE PORT INLET

(75) Inventors: Xiaohua Cai, Needham, NH (US); Handani Winarta, Nashua, MA (US); Andy Vo, Somerville, MA (US); Chung Chang Young, Weston, MA (US)

(73) Assignee: Nova Biomedical Corporation, Waltham, MA (US)

( * ) Notice: Subject to any disclaimer, the term of this patent is extended or adjusted under 35 U.S.C. 154(b) by 372 days.

This patent is subject to a terminal disclaimer.

(21) Appl. No.: 10/126,819

(22) Filed: Apr. 19, 2002

(65) Prior Publication Data

US 2004/0224369 A1 Nov. 11, 2004

(51) Int. Cl.[7] ............................................. G01N 27/327
(52) U.S. Cl. .............................. 204/403.14; 204/403.03
(58) Field of Search ........................ 204/403.01–403.15

(56) References Cited

U.S. PATENT DOCUMENTS

| | | | |
|---|---|---|---|
| 3,838,033 A | 9/1974 | Mindt et al. |
| 3,979,274 A | 9/1976 | Newman |
| 4,053,381 A | 10/1977 | Hamblen et al. |
| 4,133,735 A | 1/1979 | Afromowitz et al. |
| 4,137,495 A | 1/1979 | Brown |
| 4,184,936 A | 1/1980 | Paul et al. |
| 4,185,131 A | 1/1980 | Goller et al. |
| 4,206,755 A | 6/1980 | Klein |
| 4,224,125 A | 9/1980 | Nakamura et al. |
| 4,225,410 A | 9/1980 | Pace |
| 4,233,029 A | 11/1980 | Columbus |
| 4,273,639 A | 6/1981 | Gottermeier |
| 4,301,414 A | 11/1981 | Hill et al. |
| 4,303,887 A | 12/1981 | Hill et al. |

(List continued on next page.)

FOREIGN PATENT DOCUMENTS

| | | | |
|---|---|---|---|
| EP | 096095 | 12/1983 | |
| EP | 121385 | 10/1984 | |
| EP | 136362 | 10/1985 | |
| EP | 170375 | 5/1986 | |
| EP | 255291 | 3/1988 | |
| EP | 1152239 A1 * | 7/2001 | ......... G01N/27/327 |
| WO | WO 88/03270 | 5/1988 | |

*Primary Examiner*—Alex Noguerola
(74) *Attorney, Agent, or Firm*—Robert R. Deleault, Esq.; Mesmer & Deleault, PLLC

(57) ABSTRACT

A disposable biosensor for testing a fluid sample including a laminated strip with a first and second end, a reference electrode embedded in the laminated strip proximate to the first end, at least one working electrode embedded in the laminated strip proximate to the first end and the reference electrode, an open path for receiving a fluid sample beginning from the first end and connecting to a vent spaced from the first end, the open path being sufficiently long to expose the reference electrode and the working electrode to the fluid sample, and conductive contacts located at the second end of the laminated strip. The laminated strip has a base layer with a conductive coating, a reagent holding layer, a channel forming layer and a cover having an inlet notch at the first end. The working electrode contains a reagent having an enzyme.

45 Claims, 5 Drawing Sheets

U.S. PATENT DOCUMENTS

| | | |
|---|---|---|
| 4,310,399 A | 1/1982 | Columbus |
| 4,356,074 A | 10/1982 | Johnson |
| 4,376,689 A | 3/1983 | Nakamura et al. |
| 4,413,407 A | 11/1983 | Columbus |
| 4,418,148 A | 11/1983 | Oberhardt |
| 4,454,007 A | 6/1984 | Pace |
| 4,469,110 A | 9/1984 | Slama |
| 4,473,457 A | 9/1984 | Columbus |
| 4,490,216 A | 12/1984 | McConnell |
| 4,502,938 A | 3/1985 | Covington et al. |
| 4,545,382 A | 10/1985 | Higgins et al. |
| 4,591,550 A | 5/1986 | Hafeman et al. |
| 4,654,127 A | 3/1987 | Baker et al. |
| 4,897,173 A | 1/1990 | Nankai et al. |
| 4,900,405 A | 2/1990 | Otagawa et al. |
| 5,120,420 A | 6/1992 | Nankai et al. |
| 5,141,868 A | 8/1992 | Shanks et al. |
| 5,185,256 A | 2/1993 | Nankai et al. |
| 5,264,103 A | 11/1993 | Yoshioka et al. |
| 5,266,179 A | 11/1993 | Nankai et al. |
| 5,288,636 A | 2/1994 | Pollman et al. |
| 5,354,447 A | 10/1994 | Uenoyama et al. |
| 5,382,346 A | 1/1995 | Uenoyama et al. |
| 5,395,504 A | 3/1995 | Saurer et al. |
| 5,437,999 A | 8/1995 | Diebold et al. |
| 5,496,453 A | 3/1996 | Uenoyama et al. |
| 5,508,171 A | 4/1996 | Walling et al. |
| 5,509,410 A | 4/1996 | Hill et al. |
| 5,628,890 A | 5/1997 | Carter et al. |
| 5,682,884 A | 11/1997 | Hill et al. |
| 5,708,247 A | 1/1998 | McAleer et al. |
| 5,727,548 A | 3/1998 | Hill et al. |
| 5,755,953 A | 5/1998 | Henning et al. |
| 5,759,364 A | 6/1998 | Charlton et al. |
| 5,762,770 A | 6/1998 | Pritchard et al. |
| 5,820,551 A | 10/1998 | Hill et al. |
| 5,997,817 A | 12/1999 | Crismore et al. |
| 6,287,451 B1 | 9/2001 | Winarta et al. |

\* cited by examiner

DISPOSABLE SENSOR WITH ENHANCED SAMPLE PORT INLET

BACKGROUND OF THE INVENTION

1. Field of the Invention

The present invention relates generally to electrochemical sensors that can be used for the quantification of a specific component or analyte in a liquid sample. Particularly, this invention relates to a new and improved electrochemical sensor and to a new and improved method of fabricating electrochemical sensors. More particularly, this invention relates to a disposable electrochemical sensor that is inexpensive to manufacture. Even more particularly, this invention relates to a disposable electrochemical sensor that gives accurate readings in the presence of interferents and varying red blood cells (hematocrit). Still even more particularly, this invention relates to disposable electrochemical sensors that are used for performing electrochemical assays for the accurate determination of analytes in physiological fluids.

2. Description of the Prior Art

Biosensors have been known for more than three decades. They are used to determine concentrations of various analytes in fluids. Of particular interest is the measurement of blood glucose. It is well known that the concentration of blood glucose is extremely important for maintaining homeostasis. Products that measure fluctuations in a person's blood sugar, or glucose levels have become everyday necessities for many of the nation's millions of diabetics. Because this disorder can cause dangerous anomalies in blood chemistry and is believed to be a contributor to vision loss and kidney failure, most diabetics need to test themselves periodically and adjust their glucose level accordingly, usually with insulin injections. If the concentration of blood glucose is below the normal range, patients can suffer from unconsciousness and lowered blood pressure, which may even result in death. If the fasting blood glucose concentration is higher than the normal range, it can result in vision loss, kidney failure and vascular disease. Thus, the measurement of blood glucose levels has become a daily necessity for diabetic individuals who control their level of blood glucose by insulin therapy.

Patients who are insulin dependent are instructed by doctors to check their blood-sugar levels as often as four times a day. To accommodate a normal life style to the need of frequent monitoring of glucose levels, home blood glucose testing was made available with the development of reagent strips for whole blood testing.

One type of blood glucose biosensor is an enzyme electrode combined with a mediator compound, which shuttles electrons between the enzyme and the electrode resulting in a measurable current signal when glucose is present. The most commonly used mediators are potassium ferricyanide, ferrocene and its derivatives, as well as other metal-complexes. Many sensors based on this second type of electrode have been disclosed.

However, the prior art devices suffer from various shortcomings. One of these shortcomings is interference with biosensor readings caused by other substances in the sample fluid, which can oxidize at the same potential. Prevalent among these is ascorbic acid, uric acid and acetaminophen. As these and other interfering substances oxidize, the current resulting from their oxidation is added to and indistinguishable from the current resulting from the oxidation of the blood analyte being measured. An error therefore results in the quantification of the blood analyte.

Another shortcoming is the interference caused by red blood cells (the hematocrit effect). This interference tends to cause an artificially high response rate for low hematocrit levels and, conversely, an artificially low response rate for high hematocrit levels.

Additional shortcomings of the prior art devices are that they have a more limited linear range and require a relatively large quantity of sample volume. Further, they require a relatively longer waiting time for development of a steady-state response before a reading can be achieved. Another shortcoming of biosensors having an end or side inlet for direct introduction of the blood sample to the sample chamber from the source of the blood droplet is the inadvertent blockage or partial blockage of the inlet by the blood source. Users tend to push the biosensor hard against the blood sampling point such as at the finger or the arm. Because the entrance to the capillary channel of the biosensor is small, such action typically blocks or partially blocks the inlet. The result is that (1) the blood does not enter the capillary channel at all, or (2) the blood partially enters the channel but does not fill it up sufficiently, or (3) the blood fills up the capillary channel very slowly. Under scenario (1), the meter may not be triggered and thus not reading is made. Under scenarios (2) and (3), the meter may not be triggered or it may be triggered but gives inaccurate test results due to insufficient sample or the slowness of the capillary filling action.

Each of these shortcomings may, either individually or when combined with one or more of the other shortcomings, contribute to erroneous measurement readings during analysis.

Because of the importance of obtaining accurate glucose readings, it would be highly desirable to develop a reliable and user-friendly electrochemical sensor, which does not have one or more of the drawbacks mentioned above.

Therefore, what is needed is an electrochemical sensor that incorporates an interference-correcting electrode to minimize the interference caused by oxidizable substances present in the sample fluid. What is further needed is an electrochemical sensor whose response is substantially independent of the hematocrit of the sample fluid. What is still further needed is an electrochemical sensor that requires less sample volume than previously required by the prior art. Yet, what is still further needed is an electrochemical sensor that has a wide linear measurement range; that is, a sensor having a reduced or negligible interference effect and useable over a wider glucose concentration. What is also needed is an electrochemical sensor with a modified inlet port to facilitate introduction of the sample into the sample chamber of the electrochemical sensor.

SUMMARY OF THE INVENTION

It is an object of the present invention to provide an improved electrochemical sensor that combines an enzyme and a mediator. It is a further object of the present invention to provide an electrochemical sensor that incorporates an interference-correcting electrode to minimize the interference caused by oxidizable substances present in the sample fluid. It is a further object of the present invention to provide an electrochemical sensor whose response is substantially independent of the hematocrit levels of the sample fluid. It is still another object of the present invention to provide an electrochemical sensor that has a wide linear measurement range. It is yet another object of the present invention to provide an electrochemical sensor that has a modified inlet port to facilitate sample introduction.

The present invention achieves these and other objectives by providing an electrochemical sensor that has a modified sample inlet port for facilitating sample introduction and that requires a smaller sample size and compensates for interference from oxidizable species in the sample and from varying hematocrit levels. The present invention has a laminated, elongated body having a sample fluid channel connected between an opening on one end of the laminated body and a vent hole spaced from the opening. Within the fluid channel lies at least one working electrode and a reference electrode. The working electrode and the reference electrode are each in electrical contact with separate conductive conduits. The separate conductive conduits terminate and are exposed for making an electrical connection to a reading device on the end opposite the open channel end of the laminated body.

The laminated body has a base insulating layer made from a plastic material. Several conductive conduits are delineated on the base insulating layer. The conductive conduits may be deposited on the insulating layer by screen printing, by vapor deposition, or by any method that provides for a conductive layer, which adheres to the base insulating layer. The conductive conduits may be individually disposed on the insulating layer, or a conductive layer may be disposed on the insulating layer followed by etching/scribing the required number of conductive conduits. The etching process may be accomplished chemically, by mechanically scribing lines in the conductive layer, by using a laser to scribe the conductive layer into separate conductive conduits, or by any means that will cause a break between and among the separate conductive conduits required by the present invention. The preferred conductive coatings are gold film or a tin oxide/gold film composition. It should be pointed out that although the same electrically conducting substance (gold film or tin oxide/gold film) after scoring is used as conducting material for both working electrodes and the reference electrode, this material itself cannot function as a reference electrode. To make the reference electrode work, there must be a redox reaction (e.g., $Fe(CN)_6^{3-}+e^- \rightarrow Fe(CN)_6^{4-}$) at the electrically conducting material when a potential is applied. Therefore, a redox couple or mediator must be present at the conducting material used for the reference electrode.

On top of the base insulating layer and the conductive conduits, the laminated body has a first middle insulating layer or a reagent holding layer containing cutouts for at least one working electrode and a reference electrode. If a second working electrode is included, it and the reference electrode may share the same cutout. Where three cutouts are used, each cutout corresponds to and exposes a small portion of a single conductive conduit. The cutouts for the working electrodes can be the same or different size. The cutout for the reference electrode may be the same or different size as the cutouts for the working electrodes. The placement of all of the cutouts is such that they will all co-exist within the sample fluid channel described above. This reagent holding layer is also made of an insulating dielectric material, preferably plastic, and may be made by die cutting the material mechanically or with a laser and then fastening the material to the base layer. An adhesive, such as a pressure-sensitive adhesive, may be used to secure the reagent holding layer to the base layer. Adhesion may also be accomplished by ultrasonically bonding the reagent holding layer to the base layer. The reagent holding layer may also be made by screen printing the first middle insulating layer over the base layer.

The thickness of the reagent holding layer must be of sufficient thickness for loading a sufficient amount of electrode material for use as an electrochemical sensor. Each cutout contains electrode material. The electrode material has a redox mediator with at least one of a stabilizer, a binder, a surfactant, and a buffer. At least one of the cutouts also contains an enzyme capable of catalyzing a reaction involving a substrate for the enzyme. The redox mediator is capable of transferring electrons between the enzyme-catalyzed reaction and the working electrode.

The laminated body also has a second middle insulating layer, or channel forming layer, on top of the reagent holding layer. The second middle layer is also made of a plastic insulating material and creates the sample fluid channel of the laminated body. It contains a U-shaped cutout on one end which overlays the cutouts in the reagent holding layer with the open end corresponding to the open end of the laminated body described earlier.

The laminated body of the present invention has a top layer with a vent opening and an inlet notch. The vent opening is located such that at least a portion of the vent opening overlays the bottom of the U-shaped cutout of the channel forming layer. The vent allows air within the sample fluid channel to escape as the sample fluid enters the open end of the laminated body. The inlet notch facilitates sample introduction through the inlet by creating a top inlet aperture, which is in communication with the end inlet of the sensor. In the event that the sample inlet port is inadvertently blocked by the source of the blood sample such as a finger, the inlet notch remains open for receiving the sample fluid.

The sample fluid generally fills the sample fluid channel by capillary action. In small volume situations, the extent of capillary action is dependent on the hydrophobic/hydrophilic nature of the surfaces in contact with the fluid undergoing capillary action. This is also known as the wetability of the material. Capillary forces are enhanced by either using a hydrophilic insulating material to form the top layer, or by coating at least a portion of one side of a hydrophobic insulating material with a hydrophilic substance in the area of the top layer that faces the sample fluid channel between the open end of the laminated body and the vent opening of the top layer. It should be understood that an entire side of the top layer may be coated with the hydrophilic substance and then bonded to the second middle layer.

The number of cutouts in the reagent holding layer can be one, two and three or more. To use only one cutout, the single cutout must expose portions of at least two conductive conduits. Such an arrangement allows for testing a smaller sample volume compared to a two or a three cutout embodiment. However, this embodiment lacks the interference correction features of the other embodiments.

An embodiment having two cutouts is an alternative to the single cutout version. It has one cutout serving as the working electrode and the other one serving as a reference electrode. Another embodiment of the two cutout version combines the features of making the single cutout with that of the two cutout version. One of the cutouts containing electrode material is scored into two parts, one part serving as a first working electrode and the second part serving as the reference electrode. The second cutout serves as a second working electrode. Such a design is an alternative embodiment of the preferred embodiment of the present invention. This version of the two-cutout embodiment has the interference and hematocrit correction features but also allows for measuring an even smaller sample volume than that of the three-cutout embodiment.

In the three-cutout embodiment, two cutouts contain material for the working electrodes (W1 and W2) and one for the reference electrode (R). W2 further contains the enzyme capable of catalyzing a substrate of the enzyme. The three electrodes are positioned and sized in such a way that the resistance of the fluid sample can be precisely measured and the possible carry-over from W2 is minimized. The possible electrode arrangements within the sample fluid channel may be W1-W2-R, W1-R-W2, R-W1-W2, W2-W1-R, W2-R-W1, or R-W2-W1 with the arrangement listed as the arrangement of electrodes would appear from the open end of the laminated body to the vent opening. The preferred position was found to be W1-W2-R; that is, as the sample fluid entered the open end of the laminated body, the fluid would cover W1 first, then W2, then R. The preferred position allows for the precise measurement of blood sample resistance. This is necessary for good correlation between the resistance and hematocrit level in the blood sample. The preferred position also obviates reliability and accuracy problems due to an insufficient sample fluid size. The meter will not be triggered until the sample reaches the R. Such an arrangement also obviates possible carryover problems from enzyme-loaded working electrode (W2) to non-enzyme-loaded working electrode (W1).

As mentioned earlier, oxidizable interferents such as ascorbic acid, uric acid and acetaminophen, to name a few, cause inaccurate readings in the output of an electrochemical biosensor. The present invention negates this effect by subtracting the current response at W1 (first working electrode) from the current response from W2 (second working electrode) to calculate the analyte concentration in the sample fluid. This is achieved by maintaining the surface area of W1 substantially equal to the surface area of W2. Also important is the composition of the reagents disposed on W1 and W2. The reagents are designed to have a minimal effect on the response of the interferences which also contributes to the accuracy of the analyte measurement.

The hematocrit interference is reduced by using a two-step process. First, the resistance (r-value) between any two electrodes is measured. The revalue is then used to estimate the hematocrit level in the sample fluid. The following equation represents this relationship:

$$r = k_1/(1-H) \qquad \text{Eq. (1)}$$

where
r is resistance value measured in Ohms or Kilo-Ohms
H is hematocrit level
$k_1$ is a constant Second, the hematocrit level value is then used to mathematically correct the enzyme concentration reading obtained from above. The following equation represents the calculation performed using the calculated hematocrit level from Eq. (1):

$$C_{corr} = C_{mea}/(k_2 + k_3 C_{mea} + (k_4 + k_5 C_{mea})(1-H)) \qquad \text{Eq. (2)}$$

where
$C_{corr}$ is the corrected analyte concentration
$C_{mea}$ is the measured analyte concentration
$k_2$–$k_5$ are constants
H is the calculated hematocrit level from Eq. (1)
Constants $K_1$–$K_5$ are derived from empirical data.

All of the advantages of the present invention will be made clearer upon review of the detailed description, drawings and appended claims.

DETAILED DESCRIPTION OF THE PREFERRED EMBODIMENT

Figure 1:
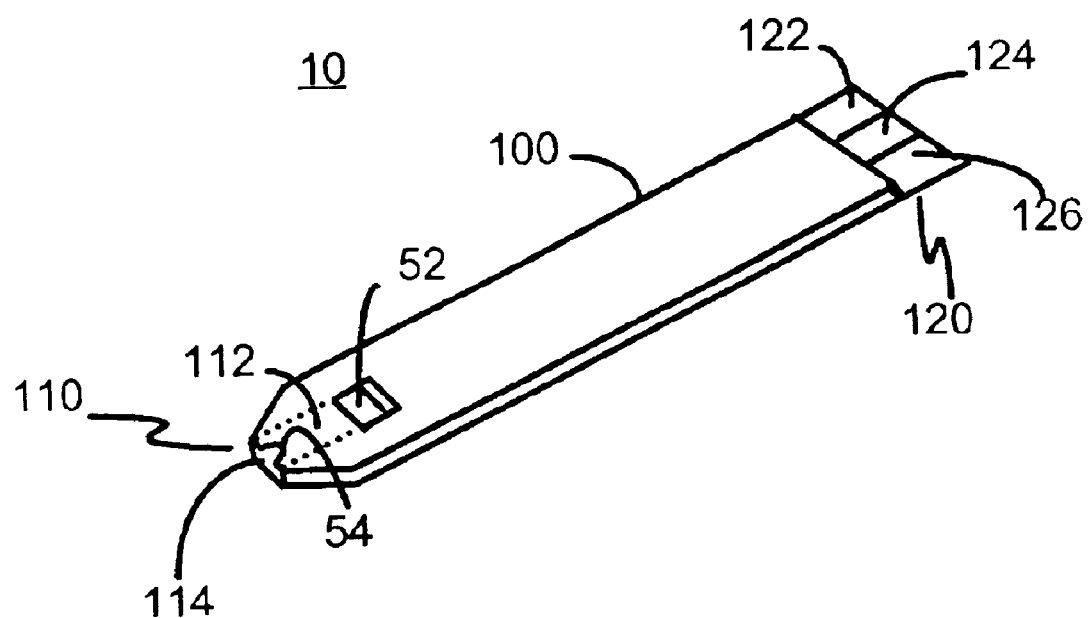
FIG. 1 is a perspective view of the present invention showing the open end, the vent and the electrical contact points of the laminated body.
Figure 2:
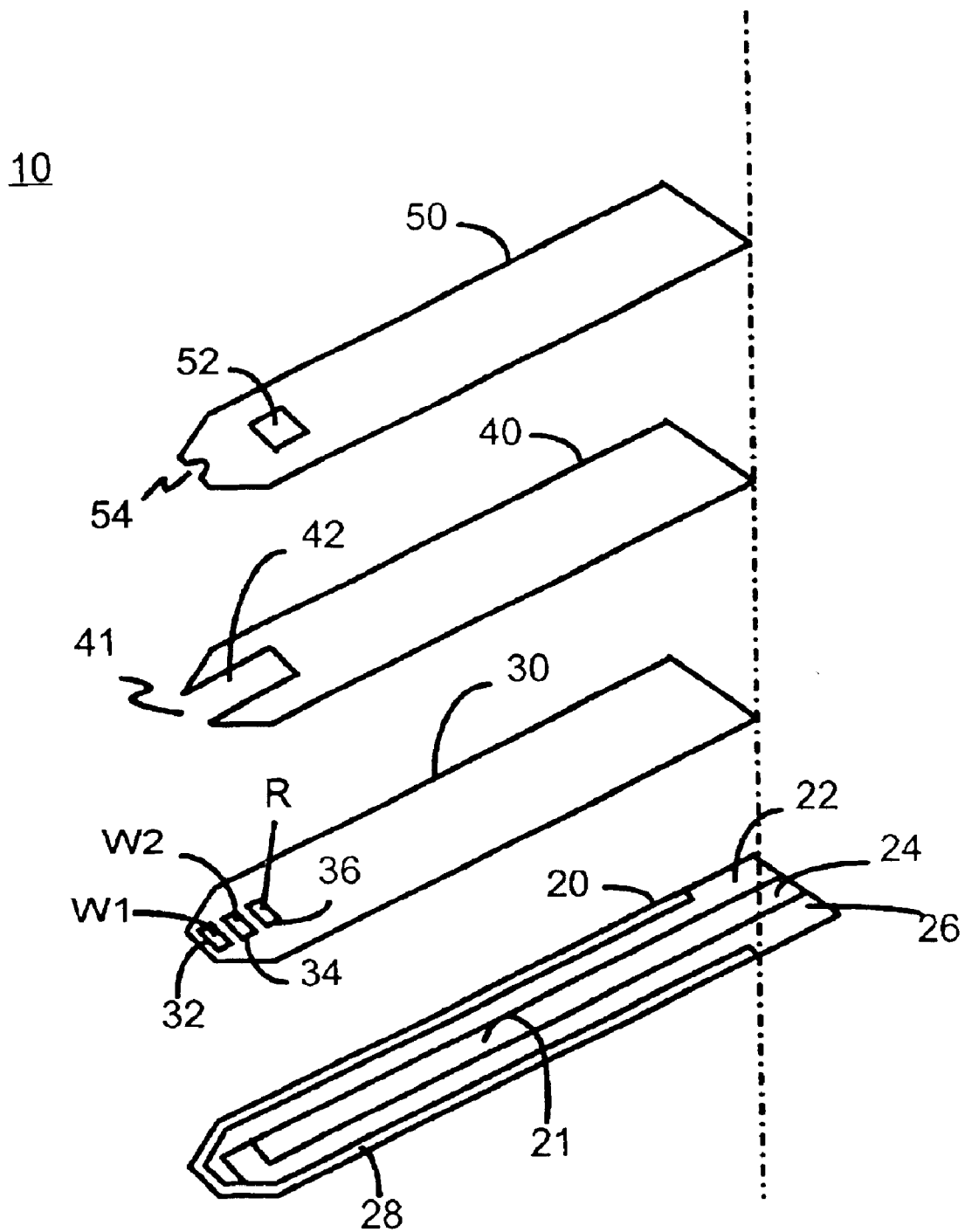
FIG. 2 is an exploded, perspective view of the present invention showing the various layers of the laminated body.
Figure 3:
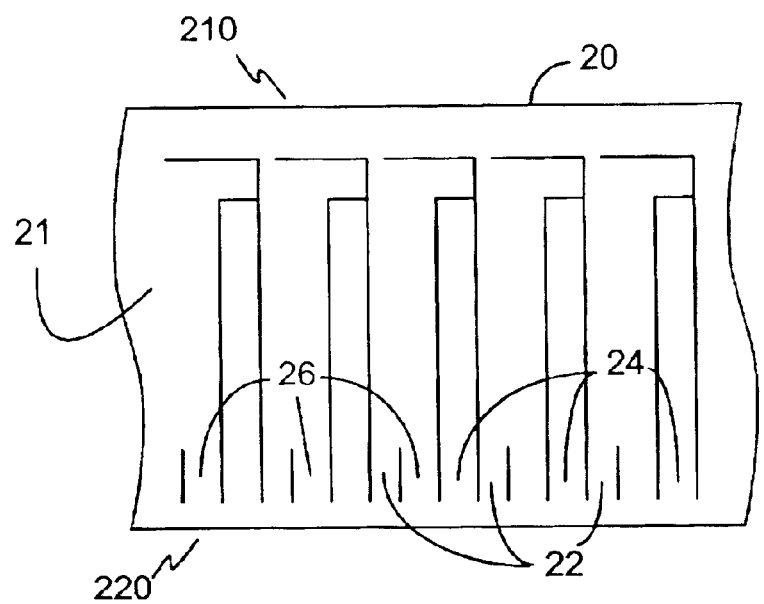
FIGS. 3A, 3B, 3C, and 3D are top views of a strip of each layer of the present invention showing the patterns for making multiple sensors of the present invention.
FIG. 3E is a top view of a segment of the laminated strip of the present invention showing the patterns for making multiple sensors of the present invention.
Figure 3:
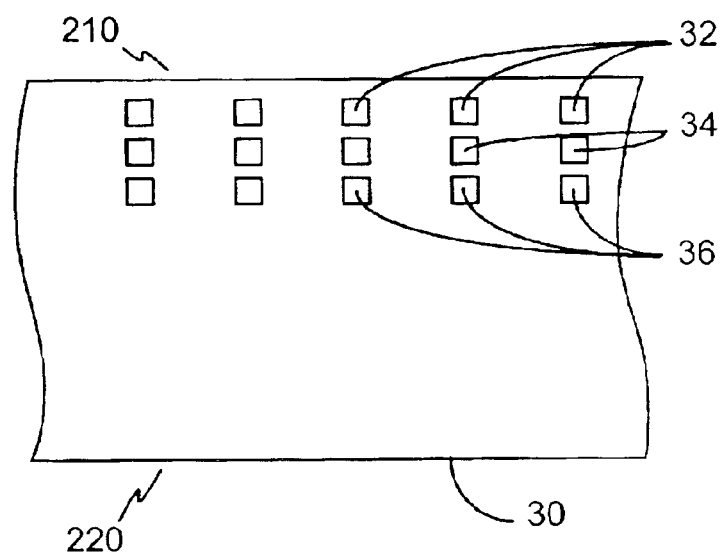
Figure 3:
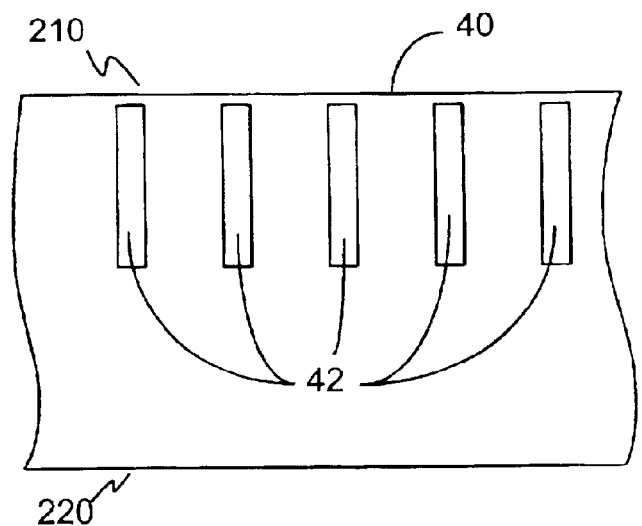
Figure 3:
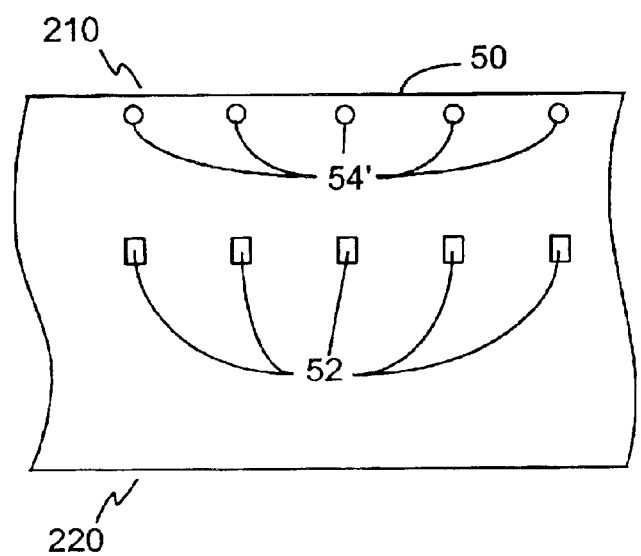
Figure 3:
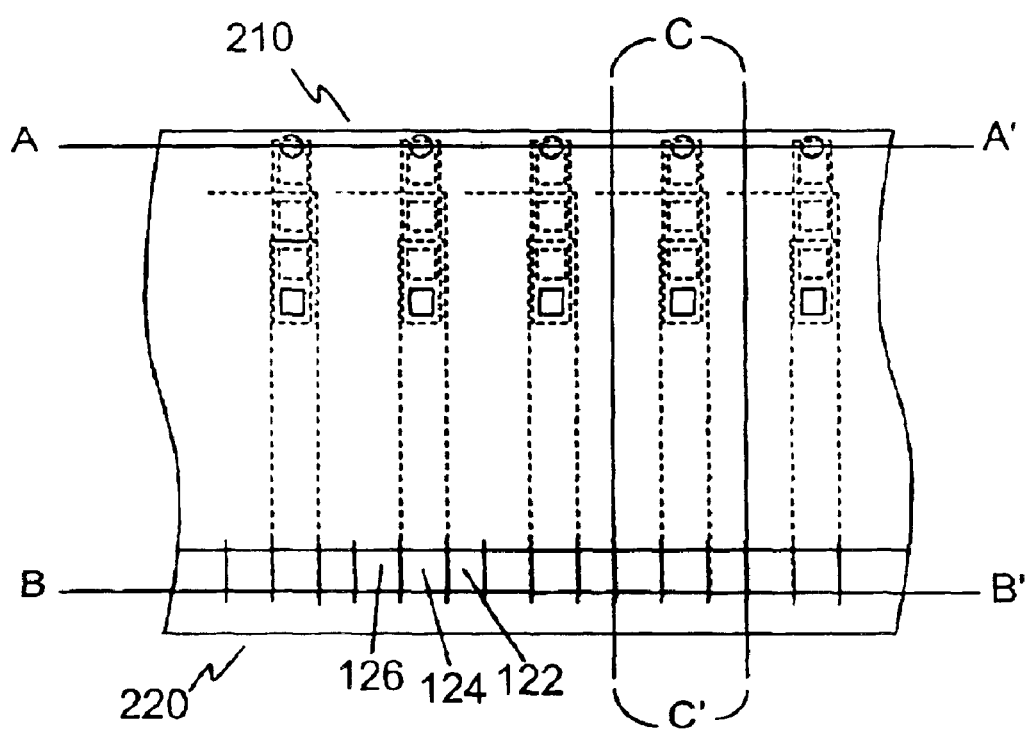

The preferred embodiment of the present invention is illustrated in FIGS. 1–3. FIG. 1 shows a sensor 10 of the present invention. Sensor 10 has a laminated body 100, a fluid sampling end 110, an electrical contact end 120, and a vent opening 52. Fluid sampling end 110 includes a sample fluid channel 112 between a sampling end aperture 114 and vent opening 52. Sampling end 110 also includes an inlet notch 54. Electrical contact end 120 has at least three discreet conductive contacts 122, 124 and 126.

Referring now to FIG. 2, laminated body 100 is composed of a base insulating layer 20, a first middle layer or reagent holding layer 30, a second middle layer or channel forming layer 40, and a top layer 50. All layers are made of a dielectric material, preferably plastic. Examples of a preferred dielectric material are polyvinyl chloride, polycarbonate, polysulfone, nylon, polyurethane, cellulose nitrate, cellulose propionate, cellulose acetate, cellulose acetate butyrate, polyester, acrylic and polystyrene. Base insulating layer 20 has a conductive layer 21 on which is delineated a first conductive conduit 22, a second conductive conduit 24 and a third conductive conduit 26. Conductive conduits 22, 24 and 26 may be formed by scribing or scoring the conductive layer 21 as illustrated in FIG. 2 or by silk-screening the conductive conduits 22, 24 and 26 onto base layer 20. Scribing or scoring of conductive layer 21 may be done by mechanically scribing the conductive layer 21 sufficiently to create the three independent conductive conduits 22, 24 and 26. The preferred scribing or scoring method of the present invention is done by using a carbon dioxide ($CO_2$) laser, a YAG laser or an eximer laser. An additional scoring line 28 (enlarged and not to scale; for illustrative purposes only) may be made, but is not necessary to the functionality of sensor 10, along the outer edge of base layer 20 in order to avoid potential static problems which could give rise to a noisy signal. Conductive layer 21 may be made of any electrically conductive material, preferably gold or tin oxide/gold. A useable material for base layer 20 is a tin oxide/gold polyester film (Cat. No. FM-1) or a gold polyester film (Cat. No. FM-2) sold by Courtaulds Performance Films, Canoga Park, Calif.

First middle layer 30 has a first electrode cutout 32 which exposes a portion of first conductive conduit 22, a second electrode cutout 34 which exposes a portion of second conductive conduit 24 and a third electrode cutout 36 which exposes a portion of third conductive conduit 26. First layer 30 is made of a plastic material, preferably a medical grade one-sided tape available from Adhesive Research, Inc., of Glen Rock, Pa. Acceptable thickness of the tape for use in the present invention are in the range of about 0.002 in. (0.051 mm) to about 0.005 in. (0.127 mm). One such tape, Arcare® 7815, is preferred because of its ease of handling and shows good performance in terms of its ability to hold a sufficient quantity of chemical reagents and to promote a favorable blood flood speed (capillary action) through sample fluid channel 112 of sensor 10. It should be understood that the use of a tape is not required. A plastic insulating layer may be coated with a pressure sensitive adhesive, or may be ultrasonically-bonded to base layer 20, or may be silk-screened onto base layer 20 to achieve the same results as using the polyester tape mentioned.

The three cutouts 32, 34 and 36 define electrode areas W1, W2 and R, respectively, and hold chemical reagents forming two working electrodes and one reference electrode. Typically, electrode area R must be loaded with a redox reagent or mediator to make the reference electrode function. If R is not loaded with a redox reagent or mediator, working electrodes W1 and W2 will not work property. The reagents preferably contain an oxidized form of a redox mediator, a stabilizer, a binder, a surfactant, and a buffer. Typically, the redox mediator may be at least one of ferrocene, potassium ferricyanide and other ferrocene derivatives. The preferred stabilizer is polyethylene glycol, the preferred binder is methyl cellulose, the preferred surfactant is t-octylphenoxypolyethoxyethanol, and the preferred buffer is a citrate buffer. Electrode area W2 is preferably loaded with the same chemical reagents loaded into electrode areas W1 and R but with the addition of an enzyme capable of catalyzing a reaction involving a substrate for the enzyme or a substrate catalytically reactive with an enzyme and a mediator capable of transferring electrons transferred between the enzyme-catalyzed reaction and the working electrode to create a current representative of the activity of the enzyme or substrate and representative of the compound. It should be pointed out that R can also be loaded with the same chemisty as W2. The enzyme could be glucose oxidase, lactate oxidase, cholesterol oxidase and creatinine amidohydrolase.

The cutouts and electrode areas of first layer 30 are positioned relative to each other and to the flow of the sample fluid in sample fluid channel 112 such that the resistance of the sample fluid may be precisely measured and the possible carryover from electrode area W2 to electrode area W1 could be minimized. Using fluid sample end 110 of sensor 10 as a reference point, the arrangements of the electrode areas could be W1-W2-R, W1-R-W2 or R-W1-W2. The preferred position was found to be W1-W2-R.

Second middle layer 40 has a U-shaped channel cutout 42 located at second layer sensor end 41. The length of channel cutout 42 is such that when second middle layer 40 is layered on top of first middle layer 30, electrode areas W1, W2 and R are within the space defined by channel cutout 42. The thickness of second middle layer 40 was found to be critical for the volume of the capillary channel and for the speed of the sample fluid flow into sample fluid channel 112, which is filled by capillary action of the sample fluid.

Top layer 50, which is placed over second middle layer 40, has a vent opening 52 spaced from fluid sample end 110 of sensor 10 to insure that sample fluid in fluid channel 112 will completely cover electrode areas W1, W2 and R. Vent opening 52 is placed in top layer 50 so that at least a portion of vent opening 52 exposes a portion of bottom of channel cutout 42 of second middle layer 40. Preferably, vent opening 52 will expose a portion of and partially overlay a portion of the U-shaped cutout 42 of second middle layer 40 that is furthest from fluid sampling end 110 of sensor 10.

Top layer 50 also includes an inlet notch 54 at fluid sample end 110 of sensor 10. Inlet notch 54 is included to facilitate sample loading in fluid channel 112 where sampling end aperture 114 could be inadvertently blocked if sample notch 54 were absent. Sample notch 54 may have any shape and is not limited to the semi-circular shape shown.

Preparation of Reagents 1 & 2

Reagents 1 and 2 comprise the oxidized form of a redox mediator, a stabilizer, a binder, a surfactant, and a buffer. Reagent 2, in addition, contains an enzyme. The oxidized form of the redox mediator, potassium ferricyanide, was found to be stable in the matrices. The quantity used in the formulation must be sufficient to attain a workable linear range. The enzyme must also have sufficient activity, purity and stability. A commercially available glucose oxidase may be obtained from Biozyme, San Diego, Calif. as Cat. No. G03A, about 270 U/mg. The stabilizer must be sufficiently water-soluble and be capable of stabilizing both the mediator and the enzyme. The binder should also be capable of binding all other chemicals in the reagents in electrode areas W1, W2 and R to the conductive surface/layer 21 of base layer 20. The preferred stabilizer is polyethylene glycol (Cat. No. P4338, Sigma Chemicals, St. Louis, Mo.). The preferred binder is Methocel 60 HG (Cat. No. 64655, Fluka Chemical, Milwaukee, Wis.). The buffer solution must have sufficient buffer capacity and pH value to optimize the enzyme reaction. A 0.05M citrate buffer is preferred. The surfactant is necessary to facilitate dispensing of Reagents 1 and 2 into cutouts 32, 34 and 36 of middle layer 30 as well as for quickly dissolving the dry chemical reagents. The amount and type of surfactant is selected to assure the previously mentioned functions and to avoid a denaturing effect on the enzyme. The preferred surfactant is Triton X-100. The reagents are prepared as follows:

Reagent 1

Step 1: Prepare 50 mM citrate buffer (pH 5.7) by dissolving 0.1512 grams citric acid and 1.2580 grams sodium citrate in 100 ml of deionized water.

Step 2: Prepare a 1% methocel 60HG solution by stirring 1 gram of methocel in 100 ml of citrate buffer from Step 1 for 12 hours.

Step 3: Add 0.3 ml of 10% Triton X-100 into the methocel solution.

Step 4: Add 2.5 grams of polyethylene glycol into the solution from Step 3.

Step 5: While stirring, add 1 gram of potassium ferricyanide to the solution from Step 4.

Reagent 2

Step 1–Step 4: same steps as Reagent 1.

Step 5: While stirring, add 6.5 grams potassium ferricyanide to the solution of Step 4.

Step 6: Add 1.0 gram of glucose oxidase to the solution of Step 5 and stir for 10 minutes or until all solid materials are completely dissolved.

Electrode Construction

A piece of a gold or tin oxide/gold polyester film available from Courtaulds Performance Films is cut to shape, as illustrated in FIG. 2, forming base layer 20 of sensor 10. A $CO_2$ laser is used to score the gold or tin oxide/gold polyester film. As illustrated in FIG. 2, the film is scored by the laser such that three electrodes at sample fluid end 110 and three contact points 122, 124 and 126 are formed at electrical contact end 120. The scoring line is very thin but sufficient to create three separate electrical conductors. A scoring line 28 can be made, but is not necessary, along the outer edge of base layer 20 to avoid potential static problems which could cause a noisy signal from the finished sensor 10.

A piece of one-sided adhesive tape is then cut to size and shape forming first middle layer 30 so that it will cover a majority of the conductive layer 21 of base layer 20 except for exposing a small electrical contact area illustrated in FIG. 1. Three rectangular, square or circular cutouts 32, 34 and 36 of substantially equal size are punched by $CO_2$ laser (25W laser available from Synrad, Inc., San Diego, Calif.). Cutouts 32, 34 and 36 define the electrode areas W1, W2 and R, which hold chemical reagents. The size of the cutouts is preferred to be made as small as possible in order to make the fluid sample channel 112 of sensor 10 as short as possible while still being capable of holding sufficient chemical reagent for the electrodes to function properly. The preferred hole size for the present invention has a typical dimension of about 0.033 in. (0.84 mm) by about 0.043 in. (1.09 mm). As illustrated in FIG. 2, cutouts 32, 34 and 36 are aligned with each other and having a spacing of about 0.028 in. (0.71 mm) between them. The rectangular cutouts are for illustrative purposes only. It should be understood that the shape of the cutouts is not critical provided that the size of the cutouts is big enough to hold sufficient chemical reagents for the electrodes to function properly but small enough to allow for a reasonably small sample channel. As noted earlier, changing the shape of the cutouts or the surface area of the cutouts may require changing the constant values $k_1$–$k_5$ for Eq. 1 and Eq. 2. As stated previously, the preferred arrangement of the electrodes formed in cutouts 32, 34 and 36 is W1 (working electrode 1), W2 (working electrode 2) and R (reference electrode).

0.4 microliters of Reagent 1 is dispensed into each electrode area W1 and R. Reagent 1 is a mixture of a redox mediator, a stabilizer, a binder, a surfactant, and a buffer. The preferred mixture for Reagent 1 is made by mixing the following components in the described percentages: about 1 wt % potassium ferricyanide, about 2.5 wt % polyethylene glycol, about 1 wt % methocel 60 HG, about 0.03 wt % Triton X-100 and about 0.05M citrate buffer (pH 5.7). 0.4 microliters of Reagent 2 is dispensed into electrode area W2.

Reagent 2 is a mixture similar to that of Reagent 1 but with the addition of an enzyme capable of catalyzing a reaction involving a substrate of the enzyme. The preferred enzyme is glucose oxidase. The preferred mixture for Reagent 2 is made by mixing the following percentages of the following ingredients: about 6.5 wt % potassium ferricyanide, about 2.5 wt % polyethylene glycol, about 1 wt % methocel 60 HG, about 0.03 wt % Triton X-100, about 0.05M citrate buffer (pH 5.7), and about 1 wt % glucose oxidase. After the addition of the reagents, the device was dried for about 2 minutes at 55° C. in an oven. After drying, a piece of double-sided tape available from Adhesive Research was fashioned into second middle layer 40 with U-shaped channel 42. Second middle layer 40 is then layered onto first middle layer 30. As mentioned earlier, this second middle layer 40 serves as a spacer and defines the size of the fluid sample channel 112. Its width and length is optimized to provide for a relatively quick moving fluid sample. The preferred size of U-shaped channel 42 is about 0.063 in. (1.60 mm) wide by about 0.248 in. (6.30 mm) long.

A piece of a transparency film (Cat. No. PP2200 or PP2500 available from 3M) is fashioned into top layer 50. A rectangular vent hole 52 and a semi-circular flu notch 54 are made using the $CO_2$ laser previously mentioned. The preferred size of vent hole 52 is about 0.075 in. (1.91 mm) by about 0.059 in. (1.50 mm). Vent hole 52 is located approximately 0.130 in. (3.3 mm) from fluid end 110 of sensor 10. Semi-circular notch 54 has a radius of approximately 0.030 in. (0.75 mm) and is recessed from fluid end 110 of sensor 10. Top layer 50 is aligned and layered onto second middle layer 40 to complete the assembly of sensor 10, as illustrated in FIG. 1.

Although the description of electrode construction above describes construction for a single sensor, the design and materials used are ideal for making multiple sensors from one piece, or a continuous strip, of each layer material as shown in FIG. 3A-3E. This would be accomplished by starting with a relative large piece of base layer 20 having conducting layer 21 thereon. A plurality of scored lines are made into conductive layer 21 such that a repetitive pattern, as illustrated in FIG. 3A, is created using the preferred scribing method described previously whereby each pattern will eventually define the three conductive paths 22, 24 and 26 for each sensor. Similarly, a large piece of first middle layer 30, which is illustrated in FIG. 3B and which also has a plurality of cutouts 32, 34, and 36 in a repetitive pattern, is sized to fit over base layer 20 in such a way that a plurality of sensors 10 will be had when completed. The size of each cutout and the electrode material disposed in the plurality of electrode areas W1, R and W2 are similar to that disclosed above. After disposing Reagents 1 & 2 in their respective cutouts and dried, a large piece of second middle layer 40 having a plurality of elongated cutouts 42 and illustrated in FIG. 3C is layered onto first middle layer 30 such that each elongated cutout 42 of second middle layer 40 contains corresponding cutouts 32, 34 and 36 of first middle layer 30. A comparably-sized top layer 50 having a plurality of vent openings 52 and notch forming openings 54' in a repetitive pattern, as shown in FIG. 3D, is layered onto second middle layer 40. FIG. 3E is a top view of the combined layers. The laminated strip created by the four layers 20, 30, 40 and 50 has a plurality of sensors 10 that can be cut from the laminated strip. The laminated strip is cut longitudinally along line A–A' at fluid sampling end 210 to form a plurality of sampling apertures 114 with sample notches 54 and longitudinally along line B–B' at electrical contact end 220 to form a plurality of conductive contacts 122, 124 and 126. The laminated strip is also cut at predetermined intervals along line C–C' forming a plurality of individual sensors 10. Shaping of the fluid sampling end 120 of each sensor 10, as illustrated in FIG. 1, may be performed if desired. It should be understood by those skilled in the art that the order in which the laminated strip can be cut is not important. For instance, the laminated strip may be cut at the predetermined intervals (C–C') and then the cuts along A–A' and B–B' can be made to complete the process.

A more inclusive description of the compensation characteristics of the present invention along with additional test parameters and examples is provided in U.S. Pat. No. 6,287,451, which is incorporated herein by reference in its entirety.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. A disposable biosensor comprising:
   a laminated strip having a first strip end, a second strip end and a vent opening spaced from said first strip end, said laminated strip comprising a base layer with at least three electrodes delineated thereon, a reagent holding layer carried on said base layer, said reagent holding layer having at least two cutouts, a channel forming layer carried on said reagent holding layer, and a cover having a notch at said first strip end;
   an enclosed channel between said first strip end and said vent opening, said enclosed channel containing said at least two cutouts;

a first reagent disposed in a first cutout of said at least two cutouts forming a reference electrode;

a second reagent disposed in a second cutout of said at least two cutouts forming a first working electrode, said second reagent containing an enzyme; and conductive contacts at said second strip end and insulated from said enclosed channel.

2. The biosensor of claim 1 wherein said enzyme is selected from the group consisting of glucose oxidase, lactate oxidase, cholesterol oxidase, and creatinine amidohydrolase.

3. The biosensor of claim 1 wherein said reagent holding layer has a third cutout.

4. The biosensor of claim 3 further comprising a third reagent disposed in said third cutout forming a second working electrode, said third reagent being substantially similar to said first reagent.

5. The biosensor of claim 1 wherein said reagents contain a redox mediator.

6. The biosensor of claim 5 wherein said reagents further contain at least one of a stabilizer, a binder, a surfactant, and a buffer.

7. The biosensor of claim 6 wherein said stabilizer is a polyalkylene glycol, said binder is a cellulose material, and said surfactant is a polyoxyethylene ether.

8. The biosensor of claim 7 wherein said stabilizer is polyethylene glycol, said binder is methyl cellulose, said surfactant is t-octylphenoxypolyethoxyethanol, and said buffer is a citrate buffer.

9. The biosensor of claim 8 wherein said reagents are made from a mixture having starting components comprising about 1 wt % to about 6.5 wt % of said redox mediator, about 2.5 wt % of said stabilizer, about 1 wt % of said binder, and about 0.03 wt % of said surfactant in said buffer.

10. The biosensor of claim 9 wherein said citrate buffer is about 0.05M.

11. The biosensor of claim 5 wherein said at least one redox mediator is potassium ferricyanide and other inorganic and organic redox mediators.

12. The biosensor of claim 9 wherein said first reagent is made of a mixture having starting components comprising about 1 wt % of said potassium ferricyanide, about 2.5 wt % of said polyethylene glycol, about 1 wt % of said methyl cellulose, about 0.03 wt % of said t-octylphenoxypolyethoxyethanol, and said citrate buffer is about 0.05M.

13. The biosensor of claim 9 wherein said second reagent is made of a mixture having starting components comprising about 6.5 wt % of said potassium ferricyanide, about 2.5 wt % of said polyethylene glycol, about 1 wt % of said methyl cellulose, about 0.03 wt % of said t-octylphenoxypolyethoxyethanol, and said pH buffer is about a 0.05M citrate buffer, and about 1 wt % of said enzyme.

14. The biosensor of claim 13 wherein said enzyme is glucose oxidase.

15. The biosensor of claim 1 wherein said base layer has a conductive coating disposed thereon for forming said at least three electrodes.

16. The biosensor of claim 15 wherein said conductive coating is gold.

17. The biosensor of claim 15 wherein said conductive coating comprising gold and tin oxide.

18. The biosensor of claim 15 wherein said base layer, said reagent holding layer, said channel forming layer, and said cover are made of a plastic dielectric material.

19. The biosensor of claim 18 wherein said plastic material is selected from the group consisting of polyvinyl chloride, polycarbonate, polysulfone, nylon, polyurethane, cellulose nitrate, cellulose propionate, cellulose acetate, cellulose acetate butyrate, polyester, acrylic, and polystyrene.

20. The biosensor of claim 1 wherein said enclosed channel is hydrophilic.

21. The biosensor of claim 1 wherein said cover has a hydrophilic coating on at least one side.

22. The biosensor of claim 1 wherein said channel forming layer has a thickness sufficient to optimize the flow of said fluid sample along said open path.

23. The biosensor of claim 22 wherein said thickness is about 0.007 inches (0.1778 mm).

24. The biosensor of claim 1 wherein the surface area of said first working electrode is substantially same as the surface area of said second working electrode.

25. A disposable electrode strip for detecting or measuring the concentration of at least one analyte in a fluid sample, said electrode strip comprising:

an insulating base layer having a first base end and a second base end;

a conductive layer disposed on one side of said base layer delineating at least three electrically-distinct conductive paths insulated from each other;

a reagent holding layer sized smaller than said base layer and overlaying a substantial portion of said conductive layer, said reagent holding layer having at least a first cutout portion and a second cutout portion spaced from said first base end, said first cutout portion exposing a limited area of a first of said at least three conductive paths and said second cutout portion exposing a limited area of a second and a third of said at least three conductive paths;

at least two electrode materials wherein a first electrode material is a reagent for measuring the concentration of said at least one analyte and wherein a second electrode material is a material suitable for use as a reference material, each of said at least two electrode materials contains at least a polyalkylene glycol as a stabilizer, said first material being disposed in said first cutout potion and said second material being disposed in said second cutout portion;

a channel forming layer sized to fit over and coextensive with said reagent holding layer, said channel forming layer having an opening configured to expose an area of said reagent holding layer a limited distance from said first base and, said area including said at least two cutout portions of said reagent holding layer; and a top layer sized to fit over and coextensive with said channel forming layer creating a sample fluid channel, said top layer having an inlet notch at a first top layer end, said first top layer end being coextensive with said first base end, and a top layer vent spaced from said first base end and configured to expose at least a small portion of said opening of said channel forming layer.

26. The strip of claim 25 wherein said sample fluid channel is hydrophillic.

27. The device of claim 25 wherein said first material and said second material further include a redox mediator, a binder, a surfactant, and a buffer.

28. The strip of claim 27 wherein said redox mediator is at least one metal complex selected from the group consisting of ferrocene, ferrocene derivatives and potassium ferricyanide, said binder is a cellulose material, said surfactant is a polyoxyethylene ether, and said buffer has a pH of about 5 to about 6.

29. The strip of claim 28 wherein said mediator is potassium ferricyanide, said stabilizer is polyethylene glycol, said binder is methyl cellulose, said surfactant is t-octylphenoxypolyethoxyethanol, and said buffer is a citrate buffer.

30. The strip of claim 29 wherein said first reagent is made of a mixture having starting components comprising about 1 wt % of said potassium ferricyanide, about 2.5 wt % of said polyethylene glycol, about 1 wt % of said methyl cellulose, and about 0.03 wt % of said t-octylphenoxypolyethoxyethanol in said citrate buffer.

31. The strip of claim 29 wherein said second reagent is made of a mixture having starting components comprising about 6.5 wt % of said potassium ferricyanide, about 2.5 wt % of said polyethylene glycol, about 1 wt % of said methyl cellulose, about 0.03 wt % of said t-octylphenoxypolyethoxyethanol, and about 1 wt % of an enzyme in said citrate buffer.

32. The strip of claim 31 wherein said enzyme is glucose oxidase.

33. The strip of claim 25 wherein said insulating base layer, said reagent holding layer, said channel forming lawyer, and said top layer are made from a plastic material selected from the group consisting of polyvinyl chloride, polycarbonate, polysulfone, nylon, polyurethane, cellulose nitrate, cellulose propionate, cellulose acetate, cellulose acetate butyrate, polyester, acrylic, and polystyrene.

34. A laminated biosensor strip comprising:
 a bass layer with an electrode end and an electrical contact end, said base layer having an electrically conductive coating on one side wherein said conductive coating has a plurality of scribed lines delineating a first conductive path having an L-shape, a second conductive path having a mirror-image L-shape wherein the L-shape ends of said first and second conduit conductive paths are adjacent to each other, and a third conductive path which is shorter than either of said first and second conductive paths and having a linear, elongated shape wherein said L-shaped ends of said first and second conductive paths and the end of said third conductive path are aligned with each other along the central axis of said base layer;
 a reagent holding layer sized smaller than said base layer and overlaying a substantial portion of said conductive coating, said reagent holding layer having at least a first cutout portion and a second cutout portion, said first cutout portion exposing a limited area of said first conductive path and said second cutout portion exposing a limited area of at least said second conductive path;
 at least two electrode materials wherein a first electrode material is a reagent for measuring the concentration of at least one analyte and wherein a second electrode material is a material suitable for use as a reference material, said first material being disposed in said first cutout portion and said second material being disposed in said second cutout portion;
 a channel forming layer sized to fit over and coextensive with said reagent holding layer, said channel forming layer having an opening configured to expose an area of said reagent holding layer that includes said at least two cutout portions of said reagent holding layer; and
 a cover with a vent, said cover disposed on and coextensive with said channel forming layer, said cover, said channel forming layer, said reagent holding layer, and said base layer forming a capillary channel with an inlet at one end and communicating with said vent at the other end.

35. The biosensor strip of claim 34 further comprising an inlet notch in said cover.

36. A disposable biosensor comprising:
 a laminated strip having a first strip end, a second strip end and a vent opening spaced from said first strip end, said laminated strip comprising a base layer with at least two electrodes delineated thereon, a reagent holding layer carried on said base layer, said reagent holding layer having at least two cutouts, a channel forming layer carried on said reagent holding layer, and a cover having a notch at said first strip end;
 an enclosed channel between said first strip end and said vent opening, said enclosed channel containing said at least two cutouts;
 a reagent disposed in said at least two cutouts forming a first working electrode and a reference electrode, said reagent containing an enzyme; and
 conductive contacts at said second strip end and insulated from said enclosed channel.

37. The biosensor of claim 36 wherein said enzyme is selected from the group consisting of glucose oxidase, lactate oxidase, cholesterol oxidase, and creatinine amidohydrolase.

38. The biosensor of claim 37 wherein said reagent further contains at least one of a redox mediator, a stabilizer, a binder, a surfactant, and a buffer.

39. The biosensor of claim 38 wherein said stabilizer is a polyalkylene glycol, said binder is a cellulose material, and said surfactant is a polyoxyethylene ether.

40. The biosensor of claim 39 wherein said stabilizer is polyethylene glycol, said binder is methyl cellulose, said surfactant is t-octylphenoxypolyethoxyethanol, and said buffer is a citrate buffer.

41. The biosensor of claim 40 wherein said reagent is made from a mixture having starting components comprising about 1 wt % to about 6.5 wt % of said redox mediator, about 2.5 wt % of said stabilizer, about 1 wt % of said binder, and about 0.03 wt % of said surfactant in said buffer.

42. The biosensor of claim 38 wherein said reagent is made from a mixture having starting components comprising about 6.5 wt % of said redox mediator, about 2.5 wt % of said stabilizer, about 1 wt % of said binder, about 0.03 wt % of said surfactant, about 1 wt % of said enzyme dissolved in a buffered solvent.

43. The biosensor of claim 42 wherein said enzyme is glucose oxidase.

44. The biosensor of claim 38 wherein said reagent is made of a mixture having stating components comprising about 6.5 wt % of potassium ferricyanide, about 2.5 wt % of polyethylene glycol, about 1 wt % of methyl cellulose, about 0.03 wt % of t-octylphenoxypolyethoxyethanol, about 1 wt % of said enzyme dissolved in said buffer wherein said buffer is about a 0.05M citrate buffer.

45. The biosensor of claim 36 wherein said reagent holding layer has a third cutout.

* * * * *